US009186640B2

(12) United States Patent
Kohane et al.

(10) Patent No.: US 9,186,640 B2
(45) Date of Patent: Nov. 17, 2015

(54) DELIVERY AND CONTROLLED RELEASE OF ENCAPSULATED LIPOPHILIC NUTRIENTS

(75) Inventors: Daniel S. Kohane, Newton, MA (US); Yoon Yeo, West Lafayette, IN (US); Peter Given, Ridgefield, CT (US); Robert S. Langer, Newton, MA (US)

(73) Assignee: PepsiCo, Inc., Purchase, NY (US)

( * ) Notice: Subject to any disclaimer, the term of this patent is extended or adjusted under 35 U.S.C. 154(b) by 1667 days.

(21) Appl. No.: 11/846,212

(22) Filed: Aug. 28, 2007

(65) Prior Publication Data

US 2009/0061048 A1    Mar. 5, 2009

(51) Int. Cl.
| | | |
|---|---|---|
| A23P 1/08 | (2006.01) | |
| A23L 1/00 | (2006.01) | |
| B01J 13/10 | (2006.01) | |
| A23L 1/0522 | (2006.01) | |
| A23L 1/053 | (2006.01) | |
| A23L 1/0562 | (2006.01) | |
| A23L 1/30 | (2006.01) | |
| A23L 1/48 | (2006.01) | |

(52) U.S. Cl.
CPC ............... *B01J 13/10* (2013.01); *A23L 1/0029* (2013.01); *A23L 1/053* (2013.01); *A23L 1/0562* (2013.01); *A23L 1/05223* (2013.01); *A23L 1/3008* (2013.01); *A23V 2002/00* (2013.01)

(58) Field of Classification Search
USPC ......................................................... 426/289
See application file for complete search history.

(56) References Cited

U.S. PATENT DOCUMENTS

| | | | |
|---|---|---|---|
| 3,803,045 A | 4/1974 | Matsukawa et al. | |
| 3,855,146 A | 12/1974 | Saeki et al. | |
| 3,869,406 A | 3/1975 | Matsukawa et al. | |
| 3,897,361 A | 7/1975 | Saeki et al. | |
| 3,919,110 A | 11/1975 | Vassiliades et al. | |
| 3,956,172 A | 5/1976 | Saeki et al. | |
| 3,965,033 A | 6/1976 | Matsukawa et al. | |
| 3,970,585 A | 7/1976 | Matsukawa et al. | |
| 4,016,098 A | 4/1977 | Saeki et al. | |
| 4,089,981 A | 5/1978 | Richardson | |
| 4,102,806 A | 7/1978 | Kondo et al. | |
| 4,156,021 A | 5/1979 | Richardson | |
| 4,590,075 A | 5/1986 | Wei et al. | |
| 4,790,998 A | 12/1988 | Swartz | |
| 4,794,000 A | 12/1988 | Ecanow | |
| 4,895,725 A | 1/1990 | Kantor et al. | |
| 4,908,233 A | 3/1990 | Takizawa et al. | |
| 4,921,644 A | 5/1990 | Lau et al. | |
| 4,923,981 A | 5/1990 | Weibel et al. | |
| 4,956,193 A | 9/1990 | Cain et al. | |
| 5,004,595 A | 4/1991 | Cherukuri et al. | |
| 5,008,254 A | 4/1991 | Weibel | |
| 5,053,240 A | 10/1991 | Todd, Jr. | |
| 5,059,416 A | 10/1991 | Cherukuri et al. | |
| 5,077,051 A | 12/1991 | Gallopo et al. | |
| 5,211,980 A | 5/1993 | Cox | |
| 5,268,190 A | 12/1993 | Gerhard | |
| 5,284,659 A | 2/1994 | Cherukuri et al. | |
| 5,338,561 A | 8/1994 | Campbell et al. | |
| 5,342,643 A | 8/1994 | Wolf et al. | |
| 5,433,960 A | 7/1995 | Meyers | |
| 5,543,162 A | 8/1996 | Timonen et al. | |
| 5,562,361 A | 10/1996 | Allen | |
| 5,591,725 A | 1/1997 | Norton | |
| 5,648,091 A | 7/1997 | Sarama et al. | |
| 5,650,190 A | 7/1997 | Buikstra et al. | |
| 5,700,397 A | 12/1997 | Maeda et al. | |
| 5,756,136 A | 5/1998 | Black et al. | |
| 5,837,308 A | 11/1998 | Campbell et al. | |
| 5,853,761 A | 12/1998 | Kumabe et al. | |
| 5,928,706 A | 7/1999 | Gibson et al. | |
| 5,952,007 A | 9/1999 | Bakker et al. | |
| 5,962,058 A | 10/1999 | Ono et al. | |
| 5,993,888 A | 11/1999 | Gibson et al. | |
| 6,010,735 A | 1/2000 | Frippiat et al. | |
| 6,039,901 A | 3/2000 | Soper et al. | |
| 6,048,562 A | 4/2000 | Mandralis et al. | |
| 6,106,875 A | 8/2000 | Soper et al. | |
| 6,180,159 B1 | 1/2001 | Villagran et al. | |
| 6,183,783 B1 * | 2/2001 | Benoit et al. | 424/497 |
| 6,187,368 B1 | 2/2001 | Gibson et al. | |
| 6,234,464 B1 | 5/2001 | Krumbholz et al. | |
| 6,309,669 B1 | 10/2001 | Setterstrom et al. | |

(Continued)

FOREIGN PATENT DOCUMENTS

| | | |
|---|---|---|
| EP | 0856355 A2 | 8/1998 |
| EP | 0970623 A2 | 1/2000 |

(Continued)

OTHER PUBLICATIONS

Degussa, Aqueous EUDRAGIT Coatings Enable GI Targeting with Capsules, Pharma Polymers, No. 8, Oct. 2001.*

(Continued)

*Primary Examiner* — D Lawrence Tarazano
*Assistant Examiner* — Philip Dubois
(74) *Attorney, Agent, or Firm* — Sterne, Kessler, Goldstein & Fox P.L.L.C.

(57) ABSTRACT

A complex coacervate delivery system is provided which encapsulates lipophilic nutrients such as, for example, fish oils high in omega-3 fatty acids. The complex coacervate delivery system protects the lipophilic nutrient from degradation, e.g., oxidation and hydrolysis, and also reduces or eliminates the unpleasant taste and odor of the lipophilic nutrient. The complex coacervate delivery system upon ingestion is operative to substantially release the lipophilic nutrient in the lower gastrointestinal tract in a pH-controlled manner. The complex coacervate delivery system may be included in a food or beverage product having a pH value within the range of about 1.5 to about 5.0.

31 Claims, No Drawings

(56) References Cited

U.S. PATENT DOCUMENTS

| | | |
|---|---|---|
| 6,315,824 B1 | 11/2001 | Lauzon |
| 6,325,859 B1 | 12/2001 | De Roos et al. |
| 6,325,951 B1 | 12/2001 | Soper et al. |
| 6,395,320 B1 | 5/2002 | Hazell et al. |
| 6,436,461 B1 | 8/2002 | Bouwmeesters et al. |
| 6,444,242 B1 | 9/2002 | Skelbaek et al. |
| 6,482,433 B1 | 11/2002 | DeRoos et al. |
| 6,500,463 B1 | 12/2002 | Van Lengerich |
| 6,514,933 B1 | 2/2003 | Young et al. |
| 6,562,361 B2 | 5/2003 | Quong |
| 6,620,571 B2 | 9/2003 | Katampe et al. |
| 6,649,207 B2 | 11/2003 | Coote et al. |
| 6,680,184 B2 | 1/2004 | Nussinovitch |
| 6,692,788 B1 | 2/2004 | Mottram et al. |
| 6,703,062 B1 | 3/2004 | Appleqvist et al. |
| 6,709,677 B2 | 3/2004 | Baichwal |
| 6,723,358 B1 | 4/2004 | Van Lengerich |
| 6,793,949 B2 | 9/2004 | Panesar |
| 6,838,109 B2 | 1/2005 | Nunes et al. |
| 6,849,185 B1 | 2/2005 | Wu et al. |
| 6,887,493 B2 | 5/2005 | Shefer et al. |
| 6,890,592 B2 | 5/2005 | Seehafer et al. |
| 6,902,743 B1 | 6/2005 | Setterstrom et al. |
| 6,913,774 B2 | 7/2005 | Cha et al. |
| 6,929,814 B2 | 8/2005 | Bouwmeesters et al. |
| 6,969,530 B1 | 11/2005 | Curtis et al. |
| 6,974,592 B2 | 12/2005 | Yan |
| 7,052,729 B2 | 5/2006 | Antheunisse et al. |
| 7,067,150 B2 | 6/2006 | Farber et al. |
| 7,094,434 B2 | 8/2006 | Gaonkar et al. |
| 7,101,585 B2 | 9/2006 | Shen et al. |
| 7,122,503 B2 | 10/2006 | Seehafer et al. |
| 7,170,670 B2 | 1/2007 | Webber |
| 7,202,006 B2 | 4/2007 | Chopra et al. |
| 7,202,991 B2 | 4/2007 | Zhang et al. |
| 7,230,750 B2 | 6/2007 | Whitesides et al. |
| 7,236,290 B1 | 6/2007 | Zhang et al. |
| 7,242,513 B2 | 7/2007 | Albert et al. |
| 7,280,266 B1 | 10/2007 | Chopra et al. |
| 7,298,543 B1 | 11/2007 | Tam et al. |
| 7,312,916 B2 | 12/2007 | Pullen et al. |
| 7,344,750 B2 | 3/2008 | Chopra et al. |
| 7,345,810 B2 | 3/2008 | Chopra et al. |
| 7,349,147 B2 | 3/2008 | Chopra et al. |
| 7,352,503 B2 | 4/2008 | Yang et al. |
| 7,375,875 B2 | 5/2008 | Whitesides et al. |
| 7,382,363 B2 | 6/2008 | Albert et al. |
| 7,391,555 B2 | 6/2008 | Albert et al. |
| 7,411,720 B2 | 8/2008 | Honeyman et al. |
| 7,417,787 B2 | 8/2008 | Chopra et al. |
| 7,426,074 B2 | 9/2008 | Tam et al. |
| 7,430,073 B2 | 9/2008 | Chopra et al. |
| 7,433,113 B2 | 10/2008 | Chopra et al. |
| 7,440,159 B2 | 10/2008 | Yang et al. |
| 2001/0016220 A1* | 8/2001 | Jager et al. ............... 426/98 |
| 2001/0041207 A1 | 11/2001 | Brown et al. |
| 2002/0039617 A1 | 4/2002 | Villagran et al. |
| 2002/0048553 A1 | 4/2002 | Baumgartner |
| 2002/0115729 A1 | 8/2002 | Yang |
| 2002/0160040 A1 | 10/2002 | Spicer et al. |
| 2003/0021878 A1 | 1/2003 | Nunes et al. |
| 2003/0072798 A1 | 4/2003 | Schwarz |
| 2003/0082272 A1 | 5/2003 | Bouwmeesters et al. |
| 2003/0096002 A1 | 5/2003 | Borek et al. |
| 2003/0104048 A1 | 6/2003 | Patel et al. |
| 2003/0109048 A1 | 6/2003 | Young et al. |
| 2003/0152629 A1 | 8/2003 | Shefer et al. |
| 2003/0152860 A1 | 8/2003 | Katampe et al. |
| 2003/0193102 A1 | 10/2003 | Yan |
| 2003/0206957 A1 | 11/2003 | Scherr |
| 2003/0224022 A1 | 12/2003 | Nussinovitch |
| 2004/0009285 A1 | 1/2004 | Antheunisse et al. |
| 2004/0017017 A1 | 1/2004 | Van Lengerich et al. |
| 2004/0032036 A1 | 2/2004 | Subramaniam et al. |
| 2004/0041306 A1 | 3/2004 | Subramaniam et al. |
| 2004/0096569 A1 | 5/2004 | Barkalow et al. |
| 2004/0103483 A1 | 6/2004 | Delplancke et al. |
| 2004/0208922 A1 | 10/2004 | Mehlhorn |
| 2004/0258803 A1 | 12/2004 | Van Benthum et al. |
| 2005/0014449 A1 | 1/2005 | Pascual et al. |
| 2005/0019416 A1 | 1/2005 | Yan |
| 2005/0042341 A1 | 2/2005 | Thomas et al. |
| 2005/0048181 A1 | 3/2005 | Gelin |
| 2005/0067726 A1 | 3/2005 | Yan et al. |
| 2005/0075497 A1 | 4/2005 | Utz et al. |
| 2005/0118130 A1 | 6/2005 | Utz et al. |
| 2005/0123757 A1 | 6/2005 | Subramaniam et al. |
| 2005/0129643 A1 | 6/2005 | Lepilleur et al. |
| 2005/0136169 A1 | 6/2005 | Haung et al. |
| 2005/0152966 A1 | 7/2005 | Borek et al. |
| 2005/0153135 A1 | 7/2005 | Popplewell et al. |
| 2005/0158547 A1 | 7/2005 | Seehafer et al. |
| 2005/0175651 A1 | 8/2005 | Simonnet et al. |
| 2005/0175757 A1 | 8/2005 | Buffet et al. |
| 2005/0202149 A1 | 9/2005 | McClements et al. |
| 2005/0203215 A1* | 9/2005 | Ugazio ................... 523/218 |
| 2005/0207993 A1 | 9/2005 | Bazemore et al. |
| 2005/0226905 A1 | 10/2005 | Tien et al. |
| 2005/0233051 A1 | 10/2005 | Shen |
| 2005/0233052 A1 | 10/2005 | Shen et al. |
| 2005/0249952 A1 | 11/2005 | Vasishtha et al. |
| 2006/0034894 A1 | 2/2006 | Lakkis et al. |
| 2006/0034936 A1 | 2/2006 | Lakkis et al. |
| 2006/0067956 A1 | 3/2006 | Kolodziejczyk et al. |
| 2006/0090769 A1 | 5/2006 | Woodson et al. |
| 2006/0165990 A1 | 7/2006 | Curtis et al. |
| 2006/0222699 A1 | 10/2006 | Gilinski |
| 2006/0240076 A1 | 10/2006 | Henson et al. |
| 2006/0251768 A1 | 11/2006 | Bouquerand |
| 2006/0275361 A1 | 12/2006 | Sakanishi et al. |
| 2007/0104795 A1 | 5/2007 | Rudhardt et al. |
| 2007/0104849 A1 | 5/2007 | McClements et al. |
| 2008/0044480 A1 | 2/2008 | Pommersheim |
| 2008/0075778 A1 | 3/2008 | Heller |
| 2008/0096964 A1* | 4/2008 | Subramanian et al. ....... 514/560 |
| 2008/0206325 A1 | 8/2008 | Bouquerand et al. |
| 2008/0227873 A1 | 9/2008 | Laneuville Ballester et al. |

FOREIGN PATENT DOCUMENTS

| | | |
|---|---|---|
| EP | 1194225 | 1/2001 |
| EP | 1585592 | 7/2004 |
| JP | 2003047432 | 2/2003 |
| WO | WO 03106014 A1 | 12/2003 |
| WO | WO 2004016720 A2 | 2/2004 |
| WO | WO 2005048998 A1 | 6/2005 |
| WO | WO 2005105290 A1 | 11/2005 |
| WO | 2007038624 A2 | 4/2007 |

OTHER PUBLICATIONS

Subramanian et al., Stabilization of Omega-3 Fatty Acids With Encapsulation Technologies, IFT Annual Meeting, 2004.*

Yeo et al., Complex Coacervates for Thermally Sensitive Controlled Release of Flavor Compounds, J. Agric. Food Chem. 2005, 53, 7518-7525.*

Trubiana, Paulo C., The Role of Speciality Food Starches in Flavor Emulsions, Flavor Technology, Amercian Chemical Society, 2005. 199-209.*

Kruif et al., Complex Coacervation of Proteins and Anionic Polysaccharides, Current Opinion in Colloid & Interface Science, 9 (2004), 340-349.*

Weinbreck et al., Microencapsulation of Oils Using Whey/Protein/Gum Arabic Coacervates, J. Microencapsul. Sep. 21, 2004 (6) 667-79, abstract.*

Gouin, Sébastien. Micro-encapsulation: Industrial Appraisal of Existing Technologies and Trends, Trends in Food Science & Technology, 2004, pp. 330-347, vol. 15, No. 7-8 [169/170], Elsevier Ltd.

Heinzelmann, Katrin et al. Microencapsulation of Fish Oil by Freeze-Drying Techniques and Influence of Process Parameters on Oxidative Stability During Storage, Eur Food Res Technol, 2000, pp. 234-239, vol. 211, Springer-Verlag.

(56) References Cited

OTHER PUBLICATIONS

Peniche, C. et al, W. Formation and Stability of Shark Liver Oil Loaded Chitosan/Calcium Alginate Capsules, Food Hydrocolloids, 2004, pp. 865-871, vol. 18, Elsevier Ltd.
Shefer, Adi et al. Novel Encapsulation System Provides Controlled Release of Ingredients, Food Technology, Nov. 2003, pp. 40-42, vol. 57, No. 11.
Strauss, George et al. Plant Phenolics as Cross-linkers of Gelatin Gels and Gelatin-based Coacervates for Use as Food Ingredients, Food Hydrocolloids, 2004, pp. 81-89, vol. 18, Elsevier Ltd.
Subramanian, Srini. Denomega Nutritional Oils: Harnessing the Power of Omega-3s, Functional Foods & Nutraceuticals, Feb. 2005, Penton Media, Inc.
Wang, Yilin et al. Effects of Salt on Polyelectrolyte-Micelle Coacervation, Macromolecules, 1999, pp. 7128-7134, vol. 32, American Chemical Society.
Kolanowski, Wojciech et al. Fish Oil Stabilization by Microencapsulation with Modified Cellulose, International Journal of Food Sciences and Nutrition, Jun. 2004, pp. 333-343, vol. 55, No. 4, Taylor & Francis Ltd.
Yeo, Yoon et al. Complex Coacervates for Thermally Sensitive Controlled Release of Flavor Compounds, Journal of Agricultural and Food Chemistry, 2005, pp. 7518-7525, vol. 53, No. 19, American Chemical Society.
Guzey Demit et al., "Impact of Electrostatic Interactions on Formation and Stability of Emulsions Containing Oil Droplets Coated by Beta-Lactoglobulin-Pectin Complexes", Journal of Agricultural and Food Chemistry, vol. 55, Dec. 19, 2006, pp. 475-485, XP002498820.
Guzey et al., "Formation, Stability and Properties of Multilayer Emulsions for Application in the Food Industry", Advances in Colloid and Interface Science, Elsevier, vol. 128-130, Feb. 26, 2007, pp. 227-248, XP005881072.
Harnsilawat et al., "Influence of pH and Ionic Strength on Formation and Stability of Emulsions Containing Oil Droplets coated by Beta-Lactoglobulin-Alginate Interfaces" Biomacromolecules, vol. 7, May 3, 2006, pp. 2052-2058, XP002498821.
Pongsawatmanit et al., "Influence of Alginate, pH and Ultrasound Treatment on Palm Oil-in-Water Emulsions Stabilized by Beta-Lactoglobulin", Colloids and Surfaces. A., Physicachemical and Engineering Aspects, Elsevier, Amsterdam, NL, Sep. 15, 2006, pp. 59-67, XP005597785.
Ribeiro A. J., et al., "Microencapsulation of Lipophilic Drugs in Chitosan-Coated Alginate Microspheres", International Journal of Pharmaceutics, Elsevier BV, NL, Sep. 30, 1999, pp. 115-123, XP001120054.
International Search Report from corresponding PCT/US2008/072854, mailing date Nov. 6, 2008.
Corresponding EP Office Action dated Sep. 6, 2010.
Office Action relating to corresponding AU Patent Application No. 2008293779.
Athlone, et al., "Flavour encapsulation and controlled release—a review," International Journal of Food Science and Technology, vol. 41, 2006 pp. 1-21, XP 002499388.
Redacted English Translation of Argentine Office Action dated Jul. 5, 2011 Relating to Corresponding Argentine Patent Application No. P080103708.
Argentine Office Action dated May 9, 2011 Relating to Corresponding Argentine Patent Application No. P080103708.
Redacted English Translation of Argentine Office Action dated Jul. 5, 2011 Relating to Corresponding Argentine Patent Application No. P080103709.
Argentine Office Action dated May 9, 2011 Relating to Corresponding Argentine Patent Application No. P080103709.
Reporting letter providing a summary of Argentine Office Action dated Sep. 7, 2011, issued in corresponding Argentine Patnt Application No. P080103708. This document is provided by the Applicant's foreign associate and the paragraphs providing legal counsel regarding the Office Action have been redacted.
Argentine Office Action dated Sep. 7, 2011, issued from corresponding Argentine Patent Application No. P080103708.
English translation of Notice of Preliminary Rejection dated Oct. 14, 2011, issued in corresponding Korean Patent Application No. 10-2010-7003309. This document was provided by the Applicant's foreign associate.
Notice of Preliminary Rejection dated Oct. 14, 2011, issued in corresponding Korean Patent Application No. 10-2010-7003309.
Reporting letter providing a summary of Argentine Office Action dated Aug. 15, 2012, issued in corresponding Argentine Patent Application No. P080103708. This document is provided by the Applicant's foreign associate and the paragraphs providing legal counsel regarding the Office Action have been redacted.
Argentine Office Action dated Aug. 15, 2012, issued from corresponding Argentine Patent Application No. P080103708.
Office Action issued for corresponding Chinese Patent Application No. 200880104590.5, dated Apr. 6, 2012.
Office Action issued for corresponding Korean Patent Application No. 10-2010-7003309, dated May 25, 2012.
Extended European Search Report dated May 2, 2012, issued for corresponding European Patent Application No. 12000252.2.
Office Action issued for corresponding Chinese Patent Application No. 200880104590.5, dated Jan. 5, 2013.
Office Action issued for corresponding European Patent Application No. 12000252.2, dated Jun. 27, 2013.
Office Action issued for corresponding Chinese Patent Application No. 200880104590.5, dated Jul. 30, 2013.
Office Action issued for corresponding European Patent Application No. 12000252.2, dated May 26, 2014.
Jan. 28, 2015 (EP)—Office Action App 12000252.2.
Mar. 17, 2015 (CN)—Office Action App. 200880104590.5.
English Translation of Office Action issued for corresponding Chinese Patent Application No. 200880104590.5. This document was provided by the Applicant's foreign associate, dated Apr. 6, 2012.
Office Action issued for corresponding Chinese Patent Application No. 200880104590.5, date Apr. 6, 2012.
English Translation of Office Action issued for corresponding Korean Patent Application No. 10-2010-7003309. This document is provided by the Applicant's foreign associate, and the paragraphs providing legal counsel regarding the Office Action have been redacted, dated May 25, 2012.
English translation of second Office Action issued for corresponding Chinese Patent Application No. 200880104590.5. This document was provided by the Applicant's foreign associate, dated Jan. 5, 2013.

* cited by examiner

DELIVERY AND CONTROLLED RELEASE OF ENCAPSULATED LIPOPHILIC NUTRIENTS

FIELD OF THE INVENTION

The present invention relates to the field of delivering lipophilic nutrients in an acidic aqueous system for controlled release to a consumer, more particularly encapsulated lipophilic nutrients in acidic aqueous systems such as food and beverage products.

BACKGROUND

Certain functional nutrients have been discovered to have beneficial health effects. Lipophilic nutrients, such as, for example, omega-3 and omega-6 fatty acids, form an important part of the human diet. These are referred to generally as "essential fatty acids," at least some of which are understood in many cases to constitute important components of cell membranes, regulate the body's use of cholesterol, and control the production of substances that affect many other bodily processes. For example, eicosapentaenoic acid (EPA) and docosahexaenoic acid (DHA), long-chain forms of omega-3 fatty acids, are understood in many cases to support brain and cardiovascular health and functions, amongst other health benefits. To increase or optimize health benefits from essential fatty acids, it has been suggested that consumption of omega-3 fatty acids should be increased.

Previously, water-insoluble lipophilic nutrients were incorporated directly into an aqueous system in one of four physical forms: a solution (with a compatible solvent), an extract, an emulsion, or a micellular dispersion (a so-called microemulsion). While all of these approaches serve to disperse the lipophilic nutrient in an aqueous system, they do not provide any additional benefits like controlled (triggered) release or extended protection against hydrolysis and oxidation. Commercially available fish oils can be high in omega-3 fatty acids, and in some cases are "encapsulated," but these commercially available fish oils have not proven physically or taste-stable in acidic food and beverage products. This results in negative hedonistic changes to the food or beverage product, such as unpleasant fishy flavors and aromas after ingestion, particularly a fishy aftertaste caused by belching fish oil from the stomach. Additionally, omega-3 fatty acids are unstable to degradation, e.g., by oxidation or hydrolysis, when exposed to air, water and/or light.

It would be desirable to provide a composition containing lipophilic nutrients which can reduce or eliminate the unpleasant taste and odor of the lipophilic nutrients, and which can be incorporated into a beverage product, food product, or other aqueous system suitable for consumption by a human or animal. It would also be desirable to provide lipophilic nutrients in a stable form for use in aqueous systems such as food and beverage products, so that the lipophilic nutrient is stable to oxidation and hydrolysis during the shelf life of the food or beverage product. It would also be desirable to provide a composition which releases lipophilic nutrients in the lower gastrointestinal tract rather than the stomach.

BRIEF SUMMARY OF THE INVENTION

Aspects of the invention are directed to delivery systems for lipophilc nutrients which may be incorporated into food and beverage products such as, for example, a ready-to-drink acidic beverage. By encapsulating the lipophilic nutrient, any negative effects (e.g., oxidation, off flavor, unpleasant aroma, etc.) can be reduced. Controlled release of the encapsulated lipophilic nutrient in the lower gastrointestinal tract reduces aftertaste, and also enhances bioavailability and overall physiological efficacy of the lipophilic nutrient.

One aspect of the invention is directed to complex coacervate delivery systems comprising an aqueous dispersion of complex coacervates. The complex coacervates have a shell comprising at least one food-grade cationic polymer and at least one food-grade anionic polymer, and a core comprising at least one lipophilic nutrient. The complex coacervate delivery system upon ingestion is operative to substantially release the lipophilic nutrient in the lower gastrointestinal tract.

Other aspects of the invention are directed to complex coacervate delivery systems comprising an aqueous dispersion of complex coacervates. The complex coacervates have a shell comprising at least one food-grade cationic polymer and at least one food-grade anionic polymer, and a core comprising at least one lipophilic nutrient. The complex coacervate delivery system is operative to substantially release the lipophilic nutrient in a pH-controlled manner.

In certain exemplary embodiments, the complex coacervate delivery systems comprise an aqueous dispersion of substantially non-agglomerated complex coacervates. The complex coacervates have a substantially non-crosslinked, substantially non-gelled shell comprising gelatin and gum acacia in a weight to weight ratio of about 4:1, and a core comprising an omega-3 fatty acid. In certain exemplary embodiments, all or at least a majority of the complex coacervates have a particle size within the range of 0.1 µm to 5.0 µm, e.g., at least a majority of the complex coacervates have a particle size within the range of 0.1 µm to 2.0 µm, or within the range of 0.3 µm to 0.5 µm. The complex coacervate delivery system is stable at pH values within the range of 2.8 to 4.0. The complex coacervate delivery system upon ingestion is operative to substantially release the omega-3 fatty acid in the lower gastrointestinal tract at a pH value within the range of about pH 6.0 and above.

Other aspects of the invention are directed to aqueous dispersions of complex coacervates. The complex coacervates have a shell comprising at least one food-grade cationic polymer and at least one food-grade anionic polymer, and a core comprising at least one lipophilic nutrient. The aqueous dispersion of complex coacervates is operative to substantially release the lipophilic nutrient in a pH-controlled manner.

Other aspects of the invention are directed to beverage products that deliver lipophilic nutrients beneficial for general health and well-being, without compromising to any significant extent the taste characteristics of the beverage product. The lipophilic nutrients can be added to beverage products having associated health benefits, as well as other beverage products that may not typically be perceived as having nutritional and health benefits, to promote healthy lifestyles. In certain exemplary embodiments, a beverage product is provided which includes a complex coacervate delivery system comprising an aqueous dispersion of complex coacervates. The complex coacervates have a shell comprising at least one food-grade cationic polymer and at least one food-grade anionic polymer, and a core comprising at least one lipophilic nutrient. The beverage product can have a pH of about 1.5 to about 5.0. Upon ingestion of the beverage product, complex coacervate delivery system is operative to substantially release the lipophilic nutrient in the lower gastrointestinal tract in a pH-controlled manner.

Other aspects of the invention are directed to food products which include a complex coacervate delivery system comprising an aqueous dispersion of complex coacervates.

The complex coacervates have a shell comprising at least one food-grade cationic polymer and at least one food-grade anionic polymer, and a core comprising at least one lipophilic nutrient. The food product can have a pH of about 1.5 to about 5.0. Upon ingestion of the food product, the complex coacervate delivery system is operative to substantially release the lipophilic nutrient in the lower gastrointestinal tract in a pH-controlled manner.

Other aspects of the invention are directed to complex coacervate delivery systems comprising an aqueous dispersion of complex coacervates. The complex coacervates have a shell comprising at least one cationic polymer and at least one anionic polymer, and a core comprising at least one lipophilic nutrient. The complex coacervate delivery system is operative to substantially release the lipophilic nutrient in a pH-controlled manner. In certain exemplary embodiments, the cationic polymer comprises at least one of Eudragit EUDRAGIT® E, EUDRAGIT® E 100, and EUDRAGIT® E PO.

These and other aspects, along with advantages and features of the present invention herein disclosed, will become apparent through reference to the following detailed description. Furthermore, it is to be understood that the features of the various embodiments described herein are not mutually exclusive and can exist in various combinations and permutations.

DETAILED DESCRIPTION

Aspects of the invention relate to complex coacervate delivery systems disclosed herein for lipophilic nutrients, which provide a stable composition suitable for inclusion in food and beverage products, that is, the complex coacervates are stable for shelf-storage, for use in making foods and beverages, and for shelf-storage when included in acidic food and beverages, etc. The complex coacervate delivery systems also provide pH-controlled release of the one or more lipophilic nutrients in the neutral to basic conditions of the lower gastrointestinal tract. That is, the complex coacervates in the complex coacervate delivery systems dissociate upon entering the part of the gastrointestinal tract below the stomach where the pH becomes substantially neutral or alkaline. As used herein, "pH-controlled release" (optionally referred to as release in a pH-controlled manner, or pH-dependent release, or pH-triggered release, or the like) means that the complex coacervates release at least the majority of the encapsulated lipophilic nutrient when the pH of the complex coacervate delivery system or the environment in which it is placed reaches or goes beyond a certain pH value, e.g., at any pH value within a specified range, or at one or more pH values within a specified range. The complex coacervate delivery system reduces or eliminates the unpleasant taste and odor of many lipophilic nutrients such as fish oil, reduces degradation, e.g. by oxidation or hydrolysis, of unstable lipophilic nutrients, and delays release of the lipophilic nutrient until the lower gastrointestinal tract, where good absorption and bioavailability occurs. The complex coacervate delivery system may be incorporated into a food or beverage product associated with health benefits, for example orange juice, to provide enhanced nutritional value. Additionally, the complex coacervate delivery system may be incorporated into food and beverage products, for example carbonated soft drinks. By encapsulating such lipophilic nutrients in a complex coacervate delivery system, possible negative hedonic, visual and physical changes to the food or beverage product may be reduced or avoided. The resulting food and beverage product is appealing to the consumer, as well as being stable and having an adequate shelf life.

In certain exemplary embodiments, a complex coacervate delivery system is provided comprising an aqueous dispersion of complex coacervates. As used herein, a "delivery system" is a composition or a mixture of components which can be used to carry the complex coacervates encapsulating the lipophilic nutrient and to provide or deliver them into a system or environment, e.g. into a food or beverage intended for consumption by humans or animals. As used herein, an "aqueous dispersion" is defined as particles distributed throughout a medium of liquid water, e.g., as a suspension, a colloid, an emulsion, a sol, etc. The medium of liquid water may be pure water, or may be a mixture of water with at least one water-miscible solvent, such as, for example, ethanol or other alcohols, propylene glycol, glycerin, dimethylsulfoxide, dimethylformamide, etc. In certain exemplary embodiments, there may be a substantial concentration of water-miscible solvent in the aqueous dispersion of the complex coacervate delivery system, such as, between about 1% and about 20% by volume, for example 5%, 10%, or 15%. In other exemplary embodiments, the complex coacervate delivery system is diluted into a beverage or food product and the concentration of water-miscible solvent is negligible. As used herein, a "complex coacervate" is a particle having a shell comprising at least two oppositely charged polymers (that is, cationic polymers of at least one type and anionic polymers of at least one type) which substantially encapsulates a core material. As used herein, polymers include not only traditional polymers, but also oligomers. At least a majority of the complex coacervates have a particle size within the range of about 0.1 μm to about 5.0 μm, preferably within the range of about 0.1 μm to about 2.0 μm, most preferably within the range of about 0.3 μm to about 0.5 μm. The particle sizes disclosed here include any or at least one value within the disclosed ranges as well as the endpoints of the ranges. Preferably, the complex coacervates are substantially non-agglomerated, but comprise a single shell encapsulating a single core. The core includes at least one water-insoluble, lipophilic nutrient, for example a liquid such as an oil. As used herein, a "lipophilic nutrient" is a substance that provides nourishment needed for life or growth or good health, which has an affinity for or is capable of dissolving in lipids, fats, oils, or non-polar solvents (e.g., a non-polar, hydrophobic substance). The shell includes a net positive charged (cationic) polymer and a net negative charged (anionic) polymer. It is believed that the net charge of each polymer is dependent on the pH of the environment and the isoelectric point of each polymer, which is in turn dependent on the density of ionizable groups in each polymer and the pKa values of those groups. Thus, disclosure here of complex coacervates comprising cationic and anionic polymers refers to the charge of the polymers in the environment or reaction conditions used for formation of the complex coacervates. Complex coacervates of the type used here are presently understood to be stabilized at least in part by the electrostatic attraction between the oppositely charged polymers, and thus are selected or designed to release upon a particular physiological trigger, specifically a pH change. In certain exemplary embodiments, the complex coacervates are not substantially additionally stabilized, for example by substantial gelling, substantial crosslinking, or substantial hardening of the complex coacervate shell. Gelling, crosslinking, and hardening are believed to hinder pH-controlled dissociation of the complex coacervates and the resulting release of lipophilic nutrients.

Exemplary polymers for use in the complex coacervates delivery systems disclosed here include oppositely charged polymers that form complex coacervates at an acidic pH, e.g., a pH value below about pH 6.0, in certain exemplary embodiments, a pH value within the range of about 1.5 to about 5.0, in certain exemplary embodiments, a pH value within the range of about 2.8 to about 4.0. The complex coacervates disclosed here are stable at an acidic pH, e.g., a pH value within the range below about pH 6.0, in certain exemplary embodiments, a pH value within the range of about 1.5 to about 5.0, in certain exemplary embodiments, a pH value within the range of about 2.8 to about 4.0. In certain exemplary embodiments, the complex coacervates are stable at a pH within such recited ranges in the sense that they are stable at any pH value within the recited range, including the endpoints. In other exemplary embodiments, the complex coacervates are stable at one or more pH values within the recited range, including the endpoints, but are not stable at every pH value within the recited range. As used herein, "stable" means that at least a majority of the complex coacervates do not dissociate and release the lipophilic nutrients. In certain exemplary embodiments, the oppositely charged cationic and anionic polymers are food-grade biopolymers. As used herein, "food-grade" is defined as any material that is deemed by the United States Food and Drug Administration to be safe for use in food and beverage products. Exemplary food-grade cationic polymers include but are not limited to proteins such as dairy proteins, including whey proteins, caseins and fractions thereof, gelatin, corn zein protein, bovine serum albumin, egg albumin, grain protein extracts, e.g. protein from wheat, barley, rye, oats, etc., vegetable proteins, microbial proteins, legume proteins, proteins from tree nuts, proteins from ground nuts, and polysaccharides such as chitosan. Other exemplary cationic polymers include but are not limited to EUDRAGIT® E, EUDRAGIT® E 100, and EUDRAGIT® E PO. EUDRAGIT® E 100 has an average molecular weight of approximately 150,000, with repeating units having the following structure:

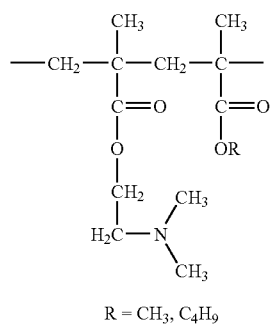

R = CH$_3$, C$_4$H$_9$

Exemplary food-grade anionic polymers include but are not limited to polysaccharides such as pectin, carrageenan, alginate, xanthan gum, modified celluloses, e.g., carboxymethylcellulose, gum acacia, gum ghatti, gum karaya, gum tragacanth, locust bean gum, guar gum, psyllium seed gum, quince seed gum, larch gum (arabinogalactans), stractan gum, agar, furcellaran, modified starches, gellan gum, fucoidan, and the like. An exemplary complex coacervate shell comprises gelatin and gum acacia. There are many possible combinations of oppositely charged polymers that are useful for forming the complex coacervates disclosed here. The weight to weight ratio of cationic polymer to anionic polymer can be from about 10:1 to about 1:10, and is preferably about 4:1.

When included in an acidic food or beverage product, e.g. a food or beverage product having a pH value within the range below about pH 6.0, in certain exemplary embodiments, a pH value within the range of about 1.5 to about 5.0, in certain exemplary embodiments, a pH value within the range of about 2.8 to about 4.0, the complex coacervate delivery systems disclosed here provide a stable dispersion of encapsulated lipophilic nutrient. Upon ingestion of the food or beverage product, that is, upon being consumed by a human or animal, the complex coacervate delivery systems are also stable and the complex coacervates do not substantially dissociate in the acidic environment of the stomach, where the pH is typically about pH 1-4. Since the lipophilic nutrient remains substantially encapsulated in the stomach, unpleasant aftertaste and bad breath from belching of free lipophilic nutrient is greatly reduced. The complex coacervate delivery system substantially releases the lipophilic nutrient in a pH-controlled manner in the lower gastrointestinal tract, e.g. the small intestine, thus enhancing bioavailability and overall physiological efficacy of the encapsulated lipophilic nutrient. It is believed that neutral to basic conditions of the lower gastrointestinal tract, e.g. typically having a pH value within the range of about pH 6.0 and above, and in certain exemplary embodiments having a pH value within the range of about pH 7.0 and above, trigger dissociation of the complex coacervates and release of the encapsulated lipophilic nutrient due to weakening of the electrostatic forces that stabilize the complex coacervate shell. It should be understood that in at least certain exemplary embodiments, the complex coacervates can release the encapsulated lipophilic nutrient in a pH-controlled manner in almost any system, for example, under in vitro conditions such as a simple aqueous dispersion at any or one or more selected pH values about 6.0 and above, or about 7.0 and above. In certain exemplary embodiments, the complex coacervates may not release the encapsulated lipophilic nutrient in a pH-controlled manner under in vitro conditions, but can undergo pH-controlled release in vivo in a human or animal lower gastrointestinal tract at any or at least one pH value about 6.0 and above or about 7.0 and above, where additional biological, chemical and/or mechanical factors act upon the complex coacervate. In addition, it is contemplated that complex coacervate delivery systems according to aspects of the present invention will exhibit additional desired physical properties. For example, it is contemplated that complex coacervate delivery systems will have an acceptable mouthfeel, taste, aroma, and appearance.

In certain exemplary embodiments, the lipophilic nutrients include fat soluble vitamins, (e.g., vitamins A, D, E, and K), tocotrienols, carotenoids, xanthophylls, (e.g., lycopene, lutein, astaxanthin, and zeazanthin), fat-soluble nutraceuticals including phytosterols, stanols and esters thereof, Coenzyme Q10 and ubiquinol, hydrophobic amino acids and peptides, essential oils and extracts, and fatty acids. Fatty acids may include, for example, conjugated linolenic acid (CLA), omega-6 fatty acids, and omega-3 fatty acids. Suitable omega-3 fatty acids include, e.g., short-chain omega-3 fatty acids such as alpha-linolenic acid (ALA), which are derived from plant sources, for example flaxseed, and long-chain omega-3 fatty acids such as eicosapentaenoic acid (EPA) and docosahexaenoic acid (DHA). The long-chain omega-3 fatty acids can be derived from, for example, marine or fish oils. Such oils can be extracted from various types of fish or marine animals, such as anchovies, capelin, cod, herring, mackerel, menhaden, salmon, sardines, shark and tuna, or from marine vegetation, such as micro-algae, or a combination thereof. Other sources of omega-3 fatty acids include liver and brain tissue and eggs.

In at least certain exemplary embodiments, at least one of EPA and DHA is included in the complex coacervate delivery system. When included as a mixture, the ratio of EPA to DHA may vary depending on the source of the omega-3 fatty acids (e.g., fish oils), the manner in which the omega-3 fatty acids are mixed, and the food or beverage product to be produced. The EPA:DHA ratio will vary to suit a particular application and can include, for example, 0:100, 100:0, 2:1, or 3:2. In certain exemplary embodiments, the mixture of omega-3 fatty acids comprises about 55-65% EPA and about 45-35% DHA. In a particular application the EPA:DHA ratio is about 60:40; however, other ratios are contemplated and within the scope of the invention.

In certain exemplary embodiments, a desired amount of a lipophilic nutrient in the above-described complex coacervate delivery system is included in a food or beverage product. The complex coacervate delivery system may be added to the food or beverage product in any number of ways, as will be appreciated by those of ordinary skill in the art given the benefit of this disclosure. In certain exemplary embodiments, the complex coacervate delivery system is sufficiently mixed in the food or beverage product to provide a substantially uniform distribution, for example a stable dispersion. Mixing should be accomplished such that the complex coacervates are not destroyed. If the complex coacervates are destroyed, oxidation of the lipophilic nutrient may result. The mixer(s) can be selected for a specific application based, at least in part, on the type and amount of ingredients used, the viscosity of the ingredients used, the amount of product to be produced, the flow rate, and the sensitivity of ingredients, such as the complex coacervate delivery system, to shear forces or shear stress.

The amount of lipophilic nutrient included in a food or beverage product may vary depending on the application and nutritional content desired. In one embodiment, the food or beverage product comprises orange juice including about 5-5000 mg of omega-3 fatty acids per 8 fluid ounces (0.24 liters) (serving size). The amount to be added will vary to suit a particular application and can be based, at least in part, on nutritional value, taste, shelf-life, efficacy levels approved, qualified health claims, and combinations thereof. Other amounts are also contemplated and within the scope of the invention. For example, it may be desired to provide at least 32 mg of omega-3 fatty acids (combined EPA and DHA) per 8 fluid ounces of the food or beverage product to meet the United States Food and Drug Administration (FDA) excellent source nutrient content claim requirements, or 16 mg per 8 fluid ounces to meet the FDA good source nutrient content claim requirements.

Encapsulation of lipophilic nutrients using the above-described complex coacervate delivery system stabilizes the lipophilic nutrient, protecting it from degradation by, for example, oxidation and hydrolysis. When included in an acidic food or beverage product, the complex coacervate delivery system can provide a stable dispersion of lipophilic nutrient over a suitable shelf-life for the food or beverage product. In certain exemplary embodiments, the finished food or beverage product including complex coacervate delivery systems disclosed here have a shelf-life greater than one week, e.g., about 1-12 months and possibly up to 24 months or longer under ambient conditions (e.g., room temperature of between 70° F. and 80° F. and controlled light exposure), depending on the level of processing the product undergoes, the type of packaging, and the materials used for packaging the product. In other embodiments, the finished product with the complex coacervate delivery system may have a shelf-life of about 12 weeks up to about 20 weeks under refrigerated conditions. In other embodiments, the finished product may be stored indefinitely under frozen conditions. Additional factors that may affect the shelf-life of the product include, for example, the nature of the base formula (e.g., an acidic beverage sweetened with sugar has a longer shelf-life than an acidic beverage sweetened with aspartame) and environmental conditions (e.g., exposure to high temperatures and sunlight is deleterious to ready-to-drink beverages).

Certain exemplary embodiments of the beverage products disclosed here include ready-to-drink beverages, beverage concentrates, syrups, shelf-stable beverages, refridgerated beverages, frozen beverages, and the like. Preferably, the beverage product is acidic, e.g. having a pH value within the range below about pH 6.0, in certain exemplary embodiments, a pH value within the range of about 1.5 to about 5.0, or in certain exemplary embodiments, a pH value within the range of about 2.8 to about 4.0.

Beverage products include but are not limited to, e.g., carbonated and non-carbonated soft drinks, fountain beverages, liquid concentrates, fruit juice and fruit juice-flavored drinks, sports drinks, energy drinks, fortified/enhanced water drinks, soy drinks, vegetable drinks, grain-based drinks (e.g. malt beverages), fermented drinks (e.g., yogurt and kefir) coffee beverages, tea beverages, dairy beverages, and mixtures thereof.

Exemplary fruit juice sources include citrus fruit, e.g. orange, grapefruit, lemon and lime, berry, e.g. cranberry, raspberry, blueberry and strawberry, apple, grape, pineapple, prune, pear, peach, cherry, mango, and pomegranate. Beverage products include bottle, can, and carton products and fountain syrup applications.

Certain exemplary embodiments of the food products disclosed here include fermented food products, yogurt, sour cream, cheese, salsa, ranch dip, fruit sauces, fruit jellies, fruit jams, fruit preserves, and the like. Preferably, the food product is acidic, e.g. having a pH value within the range below about pH 6.0, in certain exemplary embodiments, a pH value within the range of about 1.5 to about 5.0, or in certain exemplary embodiments, a pH value within the range of about 2.8 to about 4.0. All variations, alternatives, options, etc., discussed elsewhere in this disclosure apply to food embodiments of the invention, for example, any disclosed complex coacervate comprising any cationic or anionic polymer in any ratio, any lipophilic nutrients, and any particle size can be used in food embodiments in any combination suitable for application to food products.

The food or beverage product may optionally include other additional ingredients.

Optional additional ingredients include, for example, vitamins, minerals, sweeteners, flavorings, colorings, edible particulates, thickeners, emulsifiers, acidulants, electrolytes, antifoaming agents, proteins, carbohydrates, preservatives, and mixtures thereof. Other ingredients are also contemplated. The ingredients can be added at various points during processing, including before or after pasteurization, and before or after addition of the complex coacervate delivery system.

In at least certain exemplary embodiments, food and beverage products disclosed here may be pasteurized. The pasteurization process may include, for example, ultra high temperature (UHT) treatment and/or high temperature-short time (HTST) treatment. The UHT treatment includes subjecting the food or beverage product to high temperatures, such as by direct steam injection or steam infusion, or by indirect heating in a heat exchanger. Generally, after the product is pasteurized, the product can be cooled as required by the particular product composition/configuration and/or the package filling application. For example, in one embodiment, the food or beverage product is subjected to heating to about 185° F. (85° C.) to about 250° F. (121° C.) for a short period of time, for example, about 1 to 60 seconds, then cooled quickly to about 36° F. (2.2° C.)+/10° F. (5° C.) for refrigerated products, to ambient temperature for shelf stable or refrigerated products, and to about 185° F. (85° C.)±10° F. (5° C.) for hot-fill applications for shelf-stable products. The pasteurization process is typically conducted in a closed system, so as not to expose the food or beverage product to atmosphere or other possible sources of contamination. Other pasteurization or sterilization techniques may also be useful, such as, for example, aseptic or retort processing. In addition, multiple pasteurization processes may be carried out in series or parallel, as necessitated by the food or beverage product or ingredients.

Food and beverage products may, in addition, be post processed. Post processing is typically carried out following addition of the complex coacervate delivery system. Post processing can include, for example, cooling the product and filling it into container for packaging and shipping. Post processing may also include deaeration of the product to less than 4.0 ppm oxygen, preferably less than 2.0 ppm and more preferably less than 1.0 ppm oxygen. Deaeration, however, and other post processing tasks may be carried out prior to processing, prior to pasteurization, prior to mixing with the complex coacervate delivery system and/or at the same time as adding the complex coacervate delivery system. In addition, an inert gas (e.g., nitrogen or argon) headspace may be maintained during the intermediary processing of the product and final packaging.

Additionally/alternatively, an oxygen or UV barrier and/or oxygen scavengers could be used in the final packaging.

The following examples are specific embodiments of the present invention but are not intended to limit it.

EXAMPLE 1

A complex coacervate delivery system was prepared using the following methods. A 25 mL aqueous solution of 2% by weight gum acacia was prepared. Fish oil high in omega-3 fatty acid (1.3 mL) was added to the 25 mL gum acacia solution. The mixture was sonicated for two minutes, alternating pulsing on for 1 second and off for 1 second, to form an oil-in-water emulsion. Then, a 100 mL aqueous solution of 2% by weight gelatin type A pre-heated to 50° C. was added slowly to the emulsion while stirring the mixture at 500 rpm. Maintaining the temperature at 50° C., the pH was lowered to between 4.8 and 5.0 using 0.1 M phosphoric acid. Then the mixture was cooled in an ice bath. Once the temperature reached 5-10° C., the pH was lowered to between 4.0 to 4.5 using another portion of 0.1 M phosphoric acid to allow formation of coacervate complexes of cationic gelatin and anionic gum acacia encapsulating droplets of fish oil. Particle size of the complex coacervates was about 2.0 to about 3.0 µm.

It should be noted that the sonication in Example 1 could be replaced or supplemented with high-speed homogenization.

EXAMPLE 2

Fish oil high in omega-3 fatty acid (1.3 mL) was added to 25 mL aqueous solution of 0.4% by weight modified starch containing 0.83% polyvinyl alcohol, of which pH was pre-adjusted to 2.6 using citrate buffer. The mixture was sonicated for two minutes in the same manner as described in Example 1. Then, a 5 mL aqueous solution of 0.5% by weight whey protein (pH 2.6 in 10 mM citrate buffer) was added to the mixture and further sonicated for another 30 seconds. Particle size of thus formed complex coacervates was about 0.5-1 µm.

It should be noted that the modified starch in Example 2 could be replaced wholly or partly with gum acacia and/or other anionic polymers. The whey protein in Example 2 could be replaced wholly or in part with chitosan, gelatin, and/or other cationic polymers. The polyvinyl alcohol in Example 2 could be replaced wholly or partly with modified starch, polyethylene glycol, maltodextrin DE5, guar gum, and/or hydroxypropylmethylcellulose (HPMC). Also, it should be noted that the concentration of modified starch in Example 2 could be increased up to 4% by weight or more.

Also, it should be noted that the acid in Examples 1 and 2 could be selected from other organic and inorganic acids, such as, for example, phosphoric acid, ascorbic acid, citric acid, acetic acid, malic acid, tartaric acid, glucono delta-lactone, succinic acid, and any combination thereof.

EXAMPLE 3

The amount of encapsulated oil produced in Example 2 was estimated by subtracting unencapsulated oil from total oil in the system. For extracting unencapsulated free oil, the particle suspension was mixed with hexane at 1:1 ratio and spun at 14,000 rpm for 15 minutes. The hexane layer was then collected and analyzed as described in Examples 4 and 5. Total oil in the system (encapsulated oil and unencapsulated free oil) was extracted as follows. Particle suspension was brought to pH 6.7-6.8 using 1N NaOH solution and heated to 50° C. to dissolve the coacervate coats surrounding oil droplets. The suspension was mixed with hexane at 1:1 ratio and spun at 14,000 rpm for 15 minutes. The hexane layer was then collected and analyzed as described in Examples 4 and 5.

EXAMPLE 4

Five ml of methylating reagent ($BCl_3$-methanol) was added to 2 ml of hexane layer collected as described in Example 3, mixed well by shaking, and then placed in a heat block and heated at 60° C. for 10 min. The methylated solution was allowed to return to room temperature, mixed for 1 min. using a vortex mixer, and left until two layers (hexane and water) separated. The top layer was transferred into a glass vial, to which an equal volume of internal standard (0.01 mg/ml methyl laurate in hexane) was added prior to GC/MS analysis.

EXAMPLE 5

Methylated omega-3 fatty acids were analyzed using the Agilent 5973N GC/MS. One µl of each sample was injected onto the column (Restek Rtx-1, Crossbond 100% dimethyly-polysiloxane, 30 m×250 µm×1.00 µm) that was programmed for a 5 min. solvent delay at 100° C., followed by heating to 250° C. at a rate of 20° C./min., holding at 250° C. for 5 min., and then heating to 320° C. at a rate of 20° C./min. Helium was used as a carrier gas and flowed at 1 ml/min.

EXAMPLE 6

A complex coacervate delivery system was prepared in the same way as in Example 1, by replacing the gum acacia solution with a 5% by weight aqueous solution of modified starch, and replacing the gelatin solution with a 0.5% by weight aqueous solution of whey protein. No apparent difference was observed whether starting with modified starch or whey protein.

EXAMPLE 7

A complex coacervate delivery system was prepared in the same way as Example 1 with weighting agents added to the fish oil to increase its density. Exemplary weighting agents include ester gum, sucrose acetate isobutyrate, and brominated vegetable oil, among others.

EXAMPLE 8

A complex coacervate delivery system was prepared in the same way as Example 1 with a 5% by weight aqueous solution of polyvinylalcohol added.

EXAMPLE 9

A complex coacervate delivery system was prepared in the same way as in Example 1, replacing the gelatin and gum acacia solutions with a 0.083% by weight aqueous solution of chitosan, a 0.33% by weight aqueous solution of modified starch, and a 0.67% by weight aqueous solution of polyvinylalcohol.

EXAMPLE 10

EUDRAGIT® E polymers can be used as the cationic polymer in Examples 1 and 2. In this case, the EUDRAGIT® E polymer is first dissolved in ethanol, then the ethanolic solution is added to the coacervation system, of which the pH is pre-adjusted to less than pH 5.0. Once the complex coacervates form, 90-95% of ethanol in the system is removed by ultrafiltration. Alternatively, EUDRAGIT® E polymers can be dissolved in any other water-miscible organic solvents, such as, for example, other alcohols, propylene glycol, glycerin, dimethylsulfoxide, or dimethylformamide. Alternatively, EUDRAGIT® E polymers can be dissolved in acidic aqueous solutions with a pH less than pH 5.0. The acidic aqueous solution can be prepared with various organic and inorganic acids, such as, for example, phosphoric acid, ascorbic acid, citric acid, acetic acid, malic acid, tartaric acid, glucono delta-lactone, succinic acid, and any combination thereof To prepare 2.0-3.0 µm complex coacervates, a 25 mL aqueous solution of 2% by weight gum acacia is prepared. Fish oil high in omega-3 fatty acid (1.3 mL) is added to the 25 mL gum acacia solution. The mixture is sonicated for two minutes, alternating pulsing on for 1 second and off for 1 second, to form an oil-in-water emulsion. The pH is lowered to between pH 4.0 to 4.5 using 0.1 M phosphoric acid. Then, a 5 mL ethanolic solution of 5% by weight EUDRAGIT® E 100 is added slowly to the emulsion while stirring the mixture at 500 rpm. Ethanol and polymers that have not participated in the complex coacervation are then removed by ultrafiltration.

EXAMPLE 11

To prepare 0.5-1 µm complex coacervates, fish oil high in omega-3 fatty acid (1.3 mL) is added to a 25 mL aqueous solution of 0.4% by weight modified starch containing 0.83% polyvinyl alcohol, of which pH is pre-adjusted to pH 2.6 using citrate buffer. The mixture is sonicated for two minutes, alternating pulsing on for 1 second and off for 1 second, to form an oil-in-water emulsion. Then, a 5 mL ethanolic solution of 0.5% by weight EUDRAGIT® E 100 is added and the mixture is further sonicated for another 30 seconds. Ethanol and polymers that have not participated in the complex coacervation are then removed by ultrafiltration.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A complex coacervate delivery system comprising an aqueous dispersion of complex coacervates, including at least single shell complex coacervates;
    wherein the single shell complex coacervates consist essentially of:
        a single shell comprising at least one food-grade cationic polymer and at least one food-grade anionic polymer; and
        a core comprising at least one lipophilic nutrient;
    wherein the complex coacervate delivery system upon ingestion, at one or more pH values within the range of pH 6.0 and above, releases the lipophilic nutrient in the lower gastrointestinal tract.

2. The complex coacervate delivery system of claim 1, which is stable at at least one pH value within the range of 1.5 to 5.0.

3. The complex coacervate delivery system of claim 1, which is stable at at least one pH value within the range of 2.8 to 4.0.

4. The complex coacervate delivery system of claim 1, wherein the lipophilic nutrient comprises at least one of fatty acids, fat soluble vitamins, vitamin A, vitamin D, vitamin E, vitamin K, tocotrienols, carotenoids, xanthophylls, lycopene, lutein, astaxanthin, zeazanthin, fat-soluble nutraceuticals, phytosterols, stanols and esters thereof, Coenzyme Q10, ubiquinol, hydrophobic amino acids and peptides, essential oils and extracts.

5. The complex coacervate delivery system of claim 4, wherein the fatty acid comprises at least one of conjugated linolenic acid (CLA), one or more omega-3 fatty acids, and one or more omega-6 fatty acids.

6. The complex coacervate delivery system of claim 5, wherein the omega-3 fatty acid comprises at least one of eicosapentaenoic acid (EPA) and docosahexaenoic acid (DHA).

7. The complex coacervate delivery system of claim 5, wherein the omega-3 fatty acid comprises 55-65% EPA and 45-35% DHA.

8. The complex coacervate delivery system of claim 1, wherein the core further comprises at least one weighting agent.

9. The complex coacervate delivery system of claim 8, wherein the weighting agent comprises at least one of ester gum, sucrose acetate isobutyrate, and brominated vegetable oil.

10. The complex coacervate delivery system of claim 1, wherein at least a majority of the single shell complex coacervates have a particle size within the range of 0.1 µm to 5.0 µm.

11. The complex coacervate delivery system of claim 1, wherein at least a majority of the single shell complex coacervates have a particle size within the range of 0.1 µm to 2.0 µm.

12. The complex coacervate delivery system of claim 1, wherein at least a majority of the single shell complex coacervates have a particle size within the range of 0.3 µm to 0.5 µm.

13. The complex coacervate delivery system of claim 1, wherein the cationic polymer comprises at least one of dairy proteins, whey proteins, caseins and fractions thereof, gelatin, corn zein protein, bovine serum albumin, egg albumin, grain protein extracts, vegetable proteins, microbial proteins, legume proteins, proteins from tree nuts, proteins from ground nuts, and chitosan.

14. The complex coacervate delivery system of claim 1, wherein the anionic polymer comprises at least one of pectin, carrageenan, alginate, xanthan gum, modified celluloses, carboxymethylcellulose, gum acacia, gum ghatti, gum karaya, gum tragacanth, locust bean gum, guar gum, psyllium seed gum, quince seed gum, larch gum (arabinogalactans), stractan gum, agar, furcellaran, modified starches, gellan gum, and fucoidan.

15. The complex coacervate delivery system of claim 1, wherein the cationic polymer comprises gelatin and the anionic polymer comprises gum acacia.

16. The complex coacervate delivery system of claim 1, wherein the weight to weight ratio of cationic polymer to anionic polymer is from 10:1 to 1:10.

17. The complex coacervate delivery system of claim 1, wherein the weight to weight ratio of cationic polymer to anionic polymer is about 4:1.

18. The complex coacervate delivery system of claim 1, wherein the single shell is substantially non-crosslinked.

19. The complex coacervate delivery system of claim 1, wherein the single shell is substantially non-gelled.

20. The complex coacervate delivery system of claim 1, wherein the single shell complex coacervates are substantially non-agglomerated.

21. A complex coacervate delivery system comprising an aqueous dispersion of complex coacervates, including at least single shell complex coacervates;
wherein the single shell complex coacervates consist essentially of:
a single shell comprising a food-grade cationic polymer and a food-grade anionic polymer; and
a core comprising at least one lipophilic nutrient;
wherein the complex coacervate delivery system, at one or more pH values within the range of pH 6.0 and above, releases the lipophilic nutrient.

22. A complex coacervate delivery system comprising an aqueous dispersion of substantially not agglomerated, complex coacervates, including at least single shell complex coacervates, wherein the single shell complex coacervates consist essentially of:
a substantially non-crosslinked, substantially non-gelled single shell comprising gelatin and gum acacia in a weight to weight ratio of about 4:1; and
a core comprising an omega-3 fatty acid;
wherein the single shell complex coacervates have a particle size of 0.1 µm to 0.5 µm;
wherein the complex coacervate delivery system has a pH value within the range of 2.8 to 4.0; and
wherein the complex coacervate delivery system upon ingestion, at one or more pH values within the range of pH 6.0 and above, releases the omega-3 fatty acid in the lower gastrointestinal tract.

23. An aqueous dispersion of complex coacervates, including at least single shell complex coacervates., wherein the single shell complex coacervates consist essentially of:
a single shell comprising at least one food-grade cationic polymer and at least one food-grade anionic polymer; and
a core comprising at least one lipophilic nutrient;
wherein the aqueous dispersion of complex coacervates, at one or more pH values within the range of pH 6.0 and above, releases the lipophilic nutrient.

24. A beverage product comprising a complex coacervate delivery system comprising an aqueous dispersion of complex coacervates, including at least single shell complex coacervates, wherein the single shell complex coacervates consist essentially of:
a single shell comprising at least one food-grade cationic polymer and at least one food-grade anionic polymer, and
a core comprising at least one lipophilic nutrient;
wherein the beverage product has a pH value within the range of 1.5 to 5.0; and
wherein upon ingestion of the beverage product, at one or more pH values within the range of pH 6.0 and above, the complex coacervate delivery system releases the lipophilic nutrient in the lower gastrointestinal tract.

25. The beverage product of claim 24, wherein the beverage product comprises a ready-to-drink beverage.

26. The beverage product of claim 24, wherein the beverage product is selected from the group consisting of carbonated beverages, non-carbonated beverages, fountain beverages, liquid concentrates, fruit juices, fruit juice-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and mixtures thereof.

27. A food product comprising a complex coacervate delivery system comprising an aqueous dispersion of complex coacervates, including at least single shell complex coacervates, wherein the single shell complex coacervates consist essentially of:
a single shell comprising at least one food-grade cationic polymer and at least one food-grade anionic polymer, and
a core comprising at least one lipophilic nutrient;
wherein the food product has a pH value within the range of 1.5 to 5.0; and
wherein upon ingestion of the food product, at one or more pH values within the range of pH 6.0 and above, the complex coacervate delivery system releases the lipophilic nutrient in the lower gastrointestinal tract.

28. The food product of claim 27, wherein the food product is selected from the group consisting of fermented food products, yogurt, sour cream, cheese, salsa, ranch dip, fruit sauces, fruit jellies, fruit jams, and fruit preserves.

29. A complex coacervate delivery system comprising an aqueous dispersion of complex coacervates, including at least single shell complex coacervates;
wherein the single shell complex coacervates consist essentially of:
a single shell comprising at least one cationic polymer and at least one anionic polymer; and
a core comprising at least one lipophilic nutrient;
wherein the complex coacervate delivery system upon ingestion, at one or more pH values within the range of pH 6.0 and above, releases the lipophilic nutrient.

30. The complex coacervate delivery system of claim 29,

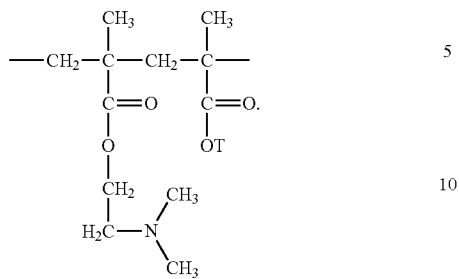

R = CH₃, C₄H₉ wherein the cationic polymer comprises.

31. The complex coacervate delivery system of claim 29, wherein the anionic polymer comprises at least one of pectin, carrageenan, alginate, xanthan gum, modified celluloses, carboxymethylcellulose, gum acacia, gum ghatti, gum karaya, gum tragacanth, locust bean gum, guar gum, psyllium seed gum, quince seed gum, larch gum (arabinogalactans), stractan gum, agar, furcellaran, modified starches, gellan gum, and fucoidan.

* * * * *